(12) United States Patent
Li et al.

(10) Patent No.: US 7,098,314 B2
(45) Date of Patent: Aug. 29, 2006

(54) **REPRODUCTION REGULATOR ENRICHED IN THE PITUITARY OF *E. COIOIDES* AND USE THEREOF**

(75) Inventors: Zhou Li, Wuhan (CN); Gui Jianfang, Wuhan (CN)

(73) Assignee: Chinese Academy of Sciences, Hubei Province (CN)

( * ) Notice: Subject to any disclaimer, the term of this patent is extended or adjusted under 35 U.S.C. 154(b) by 0 days.

(21) Appl. No.: 10/754,888

(22) Filed: Jan. 8, 2004

(65) Prior Publication Data

US 2005/0153301 A1 Jul. 14, 2005

(51) Int. Cl.
*C07K 1/00* (2006.01)
*C07K 14/00* (2006.01)

(52) U.S. Cl. ....................... 530/350; 514/12

(58) Field of Classification Search .............. 536/23.51; 435/325, 69.1; 424/130.1; 530/350
See application file for complete search history.

(56) References Cited

OTHER PUBLICATIONS

Zhang et al., "Status and Perspects of Artificial Propagation and Breeding Technique of Marine Fish in China in 1990s" Modern Fisheries Information, 2000, 15(3):3-6.

*Primary Examiner*—Robert A. Wax
*Assistant Examiner*—Marsha Tsay
(74) *Attorney, Agent, or Firm*—Fish & Richardson P.C.

(57) ABSTRACT

The present invention relates to a reproduction regulator enriched in the pituitary of *Epinephelus coioides*, DNA sequence and use thereof. The present invention also relates to expression vectors comprising the disclosed sequence and the use of the sequence to regulate reproduction, gonad differentiation and sex reversal in fish, including *E. coioides*.

18 Claims, 4 Drawing Sheets

SEQUENCE LISTING

<160> NUMBER OF SEQ ID NOS: 12

<210> SEQ ID NO 1
<211> LENGTH: 560
<212> TYPE: DNA
<213> ORGANISM: Epinephelus coioides

<400> SEQUENCE: 1
gactgtctga aagcttattg gtaccaaaac atgaagggac tgagcttggt tctcctcgtg     60
cttctcctga tgctcgccgt cggggagggc aatgatccag aaatgcagta ttggacatgt    120
gggtatagag gactctgcag acggttctgc catgcccagg agtacatcgt tggtcatcac    180
ggttgccctc ggagatacag atgctgtgct gtgcggtctt agcacctgca tgcaccagca    240
tgaggactga catctccagg taactgacga cggcgctctt ccggataacc catttcaaca    300
accttactct caatcgacac ctcttggact tctaacacgc tgtgggatgt gacaatgagt    360
gctttggaag tggacttcaa ctagttagac ctgacttatt cacagctaga tgtgcagcag    420
atgtgtaact gttgcttgat cctgtatctc acctttaata acatttataa tcactccttt    480
gtgaacagtc agttgtactc tctgaaatgc agtgttgcca ataaatgcac gaaaaaaaaa    540
aaaaaaaaaa aaaaaaaaa                                                 560

<210> SEQ ID NO 2
<211> LENGTH: 63
<212> TYPE: PRT
<213> ORGANISM: Epinephelus coioides

<400> SEQUENCE: 2

Met Lys Gly Leu Ser Leu Val Leu Leu Val Leu Leu Leu Met Leu Ala
1               5                   10                  15

Val Gly Glu Gly Asn Asp Pro Glu Met Gln Tyr Trp Thr Cys Gly Tyr
            20                  25                  30

Arg Gly Leu Cys Arg Arg Phe Cys His Ala Gln Glu Tyr Ile Val Gly
        35                  40                  45

His His Gly Cys Pro Arg Arg Tyr Arg Cys Cys Ala Val Arg Ser
    50                  55                  60

<210> SEQ ID NO 3
<211> LENGTH: 57
<212> TYPE: DNA
<213> ORGANISM: Artificial Sequence
<220> FEATURE:

```
<223> OTHER INFORMATION: primer
<220> FEATURE:
<221> NAME/KEY: misc_feature
<222> LOCATION: 56-57
<223> OTHER INFORMATION: n = a, g, c, or t

<400> SEQUENCE: 3
aagcagtggt aacaacgcag agtactttttt tttttttttt tttttttttt tttttnn       57

<210> SEQ ID NO 4
<211> LENGTH: 30
<212> TYPE: DNA
<213> ORGANISM: Artificial Sequence
<220> FEATURE:
<223> OTHER INFORMATION: primer

<400> SEQUENCE: 4
aagcagtggt aacaacgcag agtacgcggg                                      30

<210> SEQ ID NO 5
<211> LENGTH: 23
<212> TYPE: DNA
<213> ORGANISM: Artificial Sequence
<220> FEATURE:
<223> OTHER INFORMATION: primer

<400> SEQUENCE: 5
aagcagtggt aacaacgcag agt                                             23

<210> SEQ ID NO 6
<211> LENGTH: 17
<212> TYPE: DNA
<213> ORGANISM: Artificial Sequence
<220> FEATURE:
<223> OTHER INFORMATION: primer

<400> SEQUENCE: 6
caggaaacag ctatgac                                                    17

<210> SEQ ID NO 7
<211> LENGTH: 16
<212> TYPE: DNA
<213> ORGANISM: Artificial Sequence
<220> FEATURE:
<223> OTHER INFORMATION: primer

<400> SEQUENCE: 7
gtaaacgacg gccagt                                                     16

<210> SEQ ID NO 8
<211> LENGTH: 30
<212> TYPE: DNA
<213> ORGANISM: Artificial Sequence
<220> FEATURE:
<223> OTHER INFORMATION: primer

<400> SEQUENCE: 8
gaattcatat gaagggactg agcttggttc                                      30

<210> SEQ ID NO 9
<211> LENGTH: 27
<212> TYPE: DNA
<213> ORGANISM: Artificial Sequence
<220> FEATURE:
<223> OTHER INFORMATION: primer

<400> SEQUENCE: 9
```

```
gctcgagcta agaccgcaca gcacagc                                          27

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
gtgcactggt cttcaggggt t                                                21

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
gggaagtgga tgcgtgggta t                                                21

<210> SEQ ID NO 12
<211> LENGTH: 189
<212> TYPE: DNA
<213> ORGANISM: Epinephelus coioides

<400> SEQUENCE: 12
atgaagggac tgagcttggt tctcctcgtg cttctcctga tgctcgccgt cggggagggc      60
aatgatccag aaatgcagta ttggacatgt gggtatagag gactctgcag acggttctgc     120
catgcccagg agtacatcgt tggtcatcac ggttgccctc ggagatacag atgctgtgct     180
gtgcggtct                                                            189
```

REPRODUCTION REGULATOR ENRICHED IN THE PITUITARY OF E. COIOIDES AND USE THEREOF

TECHNICAL FIELD

The present invention relates to a reproduction regulator enriched in the pituitary of *Epinephelus coioides*.

BACKGROUND

*Epinephelus coioides*, a kind of marine coral reef fish, belongs to Serranidae family. For *Epinephelus* genus, the commercial market is stable and the price thereof is costly. Further, *E. coioides* is one of the marine fish whose artificial reproduction and breeding technology is the most difficult, and hitherto, the supply of breeding fry has depended on catching the wild juveniles. In the recent years, the large scale artificial reproduction of *E. coioides* has been developed in Japan, the countries in Southeast Asia, China, Taiwan and the coast of South China. With the development of large-scale artificial reproduction technology for marine fish, nature fries has not been sufficient to satisfy the need of culture production, and the artificial breeding technology has become the key technology for its continuous development. Although some primary studies on reproduction biology have been made, the basis of artificial breeding and regulation of reproduction is only very poorly understood. According to the statistics of 2000 by Qiyong ZHANG et al (QiYong Zhang and WanShu Hong, Status and perspects of artificial propagation and breeding technique of marine fish in China in 1990s. Modern fisheries information, 2000, 15(3):3–6), the *Epinephelus* species whose fry has been successfully cultivated in China include *E. akaara, E. fario, E. malabaricus, E. coioides* and the like. However, the yields obtained actually are far from the goal of stable fry batch production.

Difficulties in artificial reproduction and breeding of *E. coioides* may include the following: (1) *E. coioides* is hermaphroditic, the female matures first, then sex transformation occurs; (2) the quality of zygotes is not good and the hatching rate is low; (3) fry individuals are tenuous and captious to the bait. There are also other problems, for example, cannibalism behavior between the larvae and the juveniles, diseases, and the like. In particular, the "female to male" sex transformation process in the individual development of *E. coioides* means that the male parents are all aged, and are generally above 6 years old. The result is a relatively low proportion of juveniles in any population and bait rapidly depleted by the non-reproducing individuals. Even if male parents are caught, the fertilization rate is still very low because the sexual maturity of male and female parents is not synchronous. The present method of fry breeding is to feed, inject or imbed the heterogenous sexual steroid hormone (17a-Methyl-testosterone) to force a sex-reversal of the cultured male parents. However, the molecular mechanism of sex reversal is poorly understood, and administrating greater amounts of heterogenous steroid hormone may have disadvantages. For example, labor and time may be wasted, sea were polluted, the effectiveness of sex transformation may be poor, male sperms are weak after sex transformation, and when administration of the hormone is stopped, sex reversion occurs. Fish treated by imbedding the hormone may not take food or may take little food, and thus is detrimental to their normal development.

SUMMARY

The present invention relates to a new gene-reproduction regulator 1 (rr 1) enriched in the pituitary of *E. coioides*, having a DNA sequence of SEQ ID NO: 1.

The present invention also relates to a protein-Reproduction Regulator 1 (RR 1) enriched in the pituitary of *E. coioides*, having an amino acid sequence of SEQ ID NO: 2.

The present invention also relates to an expression vector, comprising the DNA sequence encoding said Reproduction Regulator 1.

The present invention further relates to a host cell, comprising the expression vector having the DNA sequence of said Reproduction Regulator 1.

The present invention further relates to a use of the Reproduction Regulator 1 enriched in the pituitary of *E. coioides* in the reproduction regulation of *E. coioides*.

The present invention also relates to a use of the Reproduction Regulator 1 enriched in the pituitary of *E. coioides* in the gonad differentiation of *E. coioides*.

The present invention also relates to a use of the Reproduction Regulator 1 enriched in the pituitary of *E. coioides* in the sex reversal of *E. coioides*.

The present invention also relates to a use of the Reproduction Regulator 1 enriched in the pituitary of *E. coioides* in the preparation of the artificial bait.

The present invention also relates to a use of the Reproduction Regulator 1 enriched in the pituitary of *E. coioides* in the reproduction and artificial sex control of *E. coioides*, and a use thereof in reproduction regulation, gonad differentiation and sex reversal.

The present invention also relates to a use of the Reproduction Regulator 1 as an additive in preparing the artificial bait to enhance the reproduction and artificial sex control of *E. coioides*.

The present inventor screened a new gene-reproduction regulator 1 enriched in the SMART cDNA plasmid library of the pituitary of *E. coioides*, whose expression level is very high in the pituitary. 5 colonies of the gene were detected from 90 colonies which were randomly selected and sequenced. SEQ ID NO: 2. The cDNA of the gene is 560 bp long with an open reading frame of 192 bp (nucleotides 31–222; SEQ ID NO:12) starting from the vertebrate initiation codon comprised in a motif of ANNATG. The open reading frame encodes a predicted protein of 63 amino acids. The 5' non-coding region of the sequence is 30 bp long; the 3' non-coding region is 338 bp long with a polyA tailing signal (AAUAAA) and a polyA tail. The gene has no homology with other genes and is a new gene through homology search in the GenBank. The cDNA sequence of rr1 gene (SEQ ID NO: 1) is GACTGTCTGA AAGCTTATTG GTACCAAAAC ATGAAGGGAC TGAGCTTGGT TCTCCTCGTG CTTCTCCTGA TGCTCGCCGT CGGGGAGGGC AATGATCCAG AAATGCAGTA TTGGACATGT GGGTATAGAG GACTCTGCAG ACGGTTCTGC CATGCCCAGG AGTACATCGT TGGTCATCAC GGTTGCCCTC GGAGATACAG ATGCTGTGCT GTGCGGTCTT AGCACCTGCA TGCACCAGCA TGAGGACTGA CATCTCCAGG TAACTGACGA CGGCGCTCTT CCGGATAACC CATTTCAACA ACCTTACTCT CAATCGACAC CTCTTGGACT TCTAACACGC TGTGGGATGT GACAATGAGT GCTTTGGAAG TGGACTTCAA CTAGTTAGAC CTGACTTATT CACAGCTAGA TGTGCAGCAG ATGTGTAACT GTTGCTTGAT CCTGTATCTC ACCTTTAATA ACATTTATAA TCACTCCTTT GTGAACAGTC AGTTGTACTC

TCTGAAATGC AGTGTTGCCA ATAAATGCAC GAAAAAAAAA AAAAAAAAAA AAAAAAAAAA.

The amino acid sequence (SEQ ID NO: 2) of the protein encoded by rr1 gene is MKGLSLVLLVLLLMLAVGEG-NDPEMQYWTCGYRGLCR-RFCHAQEYIVGHHGCPRRY RCCAVRS.

Analysis of the protein sequence with Signal P program showed that the 21 amino acids sequence at its N-terminal is much more likely to be a signal peptide. The predicted cleavage site for a signalase is between $21^{st}$ and $22^{nd}$ amino acids. It is therefore likely that the protein is a secreted protein (FIG. 1). Analysis of its transmembrane structure with DAS software showed that the protein exhibits a transmembrane domain at the corresponding site of the signal peptide (FIG. 2).

The mRNA level of the gene in the liver, kidney, spleen, pancreas, heart, muscle, pituitary, hypothalamus, endbrain, cerebel, midbrain and medulla oblongata of E. coioides was examined respectively using RT-PCR technology; the expression map of the gene expressed in the pituitary, hypothalamus and mature ovary during the different stages, for example, the oogenesis stage, oocyte mature stage and the sex reversal stage, and in the gonad during the sex reversal stage was examined respectively; the expression map of the gene expressed in the unfertilized egg, morula, blastula, gastrula, neurula, optic vesicle stage embryo, heartbeat beginning stage embryo, embryo prior to hatching, hatching embryo, fry hatching one day was examined respectively; the results showed that the gene is largely transcribed in the pituitary, slightly transcribed in the hypothalamus, and no transcripts was detected in other ten kinds of tissues (FIG. 3); the same high abundance in the pituitary during three kinds of different gonad development stages was detected, the same low abundance in the hypothalamus during three stages was detected, and no transcripts was detected in the mature ovary, however, there was a transcript of high abundance in the gonad during the sex reversal (FIG. 4). In order to identify the results of different expression of rr1 gene in the gonad of E. coioides, we extracted the total RNA of the gonad of E. coioides, which weighted 150 g, 450 g, 700 g, 950 g and 1600 g respectively, to perform RT-PCR analysis. The analysis of tissue section showed that the transcript of rr1 gene with high abundance in the male gonad could be detected, and a blurry expected band was amplified in the individual of 950 g, however, no transcripts were detected in other three small individuals (FIG. 5).

Meanwhile, we collected 63 specimens of E. coioides weighted 600 g to perform artificial sex reversal experiments by administrating 8 mg/Kg methyl-testosterone. All the tested specimens could be successfully induced to the male individuals and produced the sperm in the $42^{nd}$ day after the experiment. We took the gonads of two individuals to perform RT-PCR analysis every other week. As shown in FIG. 6, rr1 gene began to transcribe after administrating the hormone for 4 weeks. Similar to other vertebrates, "hypothalamus-pituitary-gonad" is the important incretion system to regulate the reproduction activities in the teleosts. The expression map of the gene is completed coincident with the three class backbone structure composed of "hypothalamus-pituitary-gonad" in the incretion regulation system of fish reproduction; meanwhile, no transcript production was detected in the mature ovary, while high abundant transcript was detected in the gonad during the sex reversal, which indicated that the gene has an important function in the regulation of the reproduction and gonad differentiation of E. coioides.

Because rr1 gene is a completely new gene, an understanding of the gene in the mankind is limited to the present inventors' research at present. The gene encodes a secreted polypeptide with a transmembrane domain, which is highly transcribed in the pituitary, slightly transcribed in the hypothalamus and no mRNA thereof is detected in the mature ovary, but it is highly transcribed in the gonad during the sex reversal. So the gene plays an important role in the reproduction regulation and gonad differentiation of E. coioides. The function of the gene in the reproduction regulation, gonad differentiation and sex reversal of E. coioides is studied by preparation of the protein expressed by prokaryote of the gene respectively. The expressed protein is soluble and can be purified quickly by Affinity chromatography, which can be used to prepare an artificial bait as a feedstuff additive to enhance the productivity and artificial control of the sex.

The advantages of the present invention are as follows: The function of the gene in the reproduction regulation, gonad differentiation and sex reversal of E. coioides is studied by preparation of the protein encoded by the said gene, and the protein is an endogenic secreted polypeptide, which can be used to prepare an artificial bait to enhance the productivity and artificial sex control by preparation of the prokaryote expressed protein.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
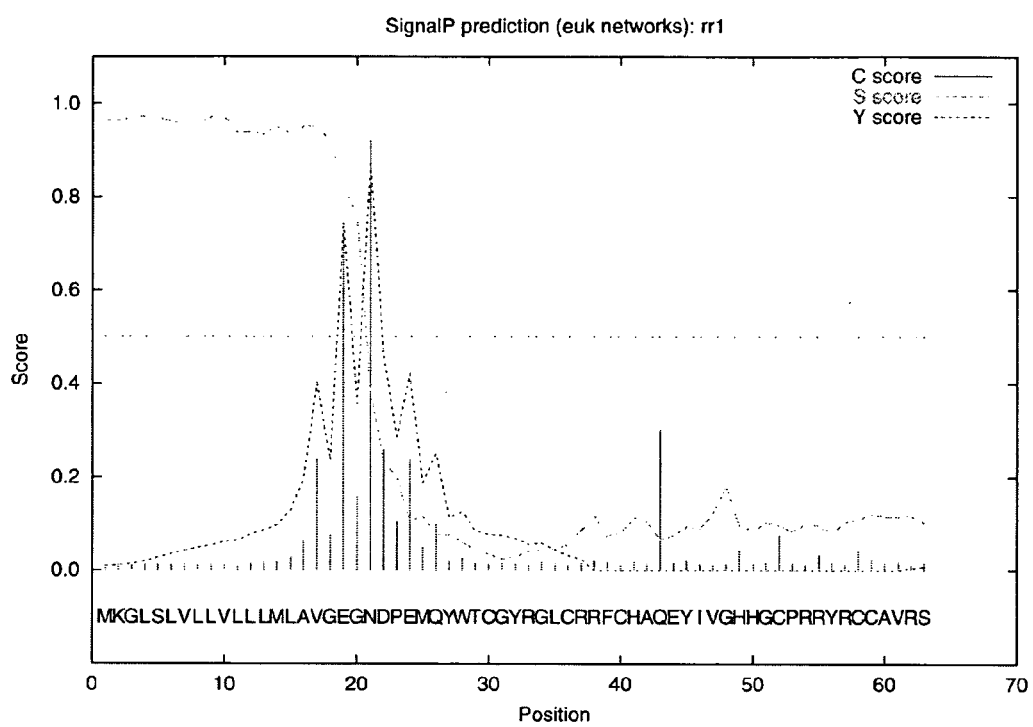
FIG. 1 illustrates the site of the signal peptide of rr1 gene as determined by the Signal P program.
Figure 2:
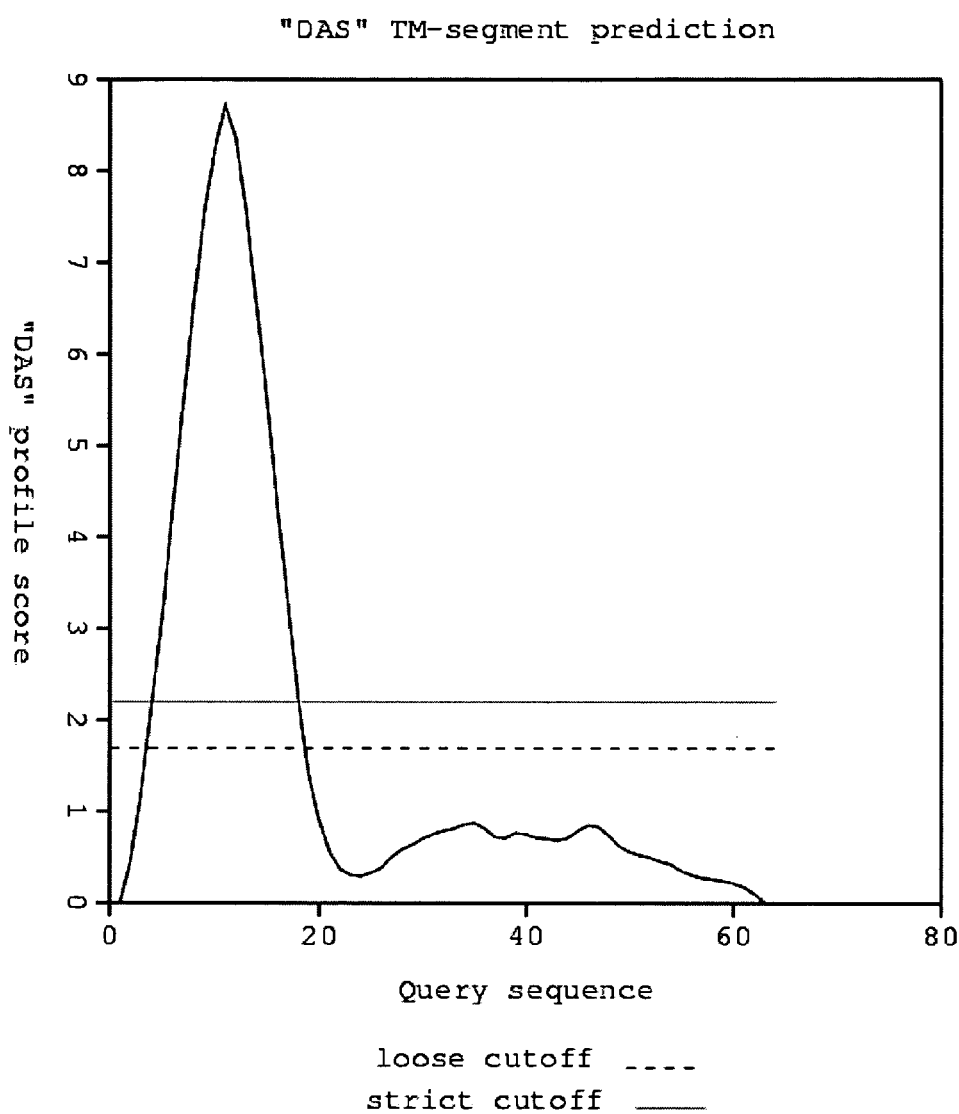
FIG. 2 shows the predicted transmembrane domain of rr1 gene as predicted with DAS.
Figure 3:
FIG. 3 shows the expression of rr1 gene in the tissues of E. coioides detected by RT-PCR, 1: liver, 2: kidney, 3: spleen, 4: pancreas, 5: heart, 6: muscle, 7: pituitary, 8: hypothalamus, 9: endbrain, 10: cerebel, 11: midbrain, 12: medulla oblongata.

The present invention provides novel polypeptides that are enriched in the pituitary of marine organisms and nucleic acids that encode such polypeptides. The invention also provides antibodies that bind to the polypeptides of the invention and methods of using such polypeptides to regulate reproduction, gonad differentiation and sex reversal in marine organisms.

In one embodiment, the invention provides an isolated polypeptide comprising the amino acid sequence of SEQ ID NO:2. An "isolated" protein or polypeptide is one that has been separated from naturally associated components that accompany it in its native state. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art. A "protein" as used herein can be a peptide or polypeptide.

The invention further provides an isolated polypeptide comprising the amino acid sequence of SEQ ID NO:2 with up to 10, 5, or 3 conservative amino acid substitutions, wherein the polypeptide comprises a transmembrane domain and is enriched in the pituitary of a vertebrate. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (see, e.g., Pearson et al. (1994) Methods in Molecular Biology 24:307–31).

The following six groups each contain amino acids that are conservative substitutions for one another:

1) Alanine (A), Serine (S), Threonine (T);
2) Aspartic Acid (D), Glutamic Acid (E);
3) Asparagine (N), Glutamine (Q);
4) Arginine (R), Lysine (K);
5) Isoleucine (I), Leucine (L), Methionine (M), Valine (V), and
6) Phenylalanine (F), Tyrosine (Y), Tryptophan (W).

The invention further provides an isolated polypeptide comprising an amino acid sequence at least 80%, 85%, 90%, or 95% identical to the amino acid sequence of SEQ ID NO:2, wherein the polypeptide comprises a transmembrane domain and is enriched in the pituitary of a vertebrate. Sequence homology for polypeptides, which is also referred to as sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof.

A polypeptide "mutein" refers to a polypeptide whose sequence contains substitutions, insertions or deletions of one or more amino acids compared to the amino acid sequence of the native or wild type protein. A mutein has at least 50% sequence homology to the wild type protein, preferred is 60% sequence homology, more preferred is 70% sequence homology. Most preferred are muteins having 80%, 90% or 95% sequence homology to the wild type protein, in which sequence homology is measured by any common sequence analysis algorithm, such as Gap or Bestfit.

The invention also provides an isolated polypeptide encoded by a nucleic acid that hybridizes under highly stringent conditions to a probe the sequence of which consists of SEQ ID NO:2, wherein the polypeptide comprises a transmembrane domain and is enriched in the pituitary of a vertebrate. Substantial homology or similarity exists when a nucleic acid or fragment thereof hybridizes to another nucleic acid, to a strand of another nucleic acid, or to the complementary strand thereof, under selective hybridization conditions. Typically, selective hybridization will occur when there is at least about 55% sequence identity—preferably at least about 65%, more preferably at least about 75%, and most preferably at least about 90%—over a stretch of at least about 14 nucleotides. See, e.g., Kanehisa (1984) Nucl. Acids Res. 12:203–213.

Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. "Stringent hybridization conditions" and "stringent wash conditions" in the context of nucleic acid hybridization experiments depend upon a number of different physical parameters. The most important parameters include temperature of hybridization, base composition of the nucleic acids, salt concentration and length of the nucleic acid. One having ordinary skill in the art knows how to vary these parameters to achieve a particular stringency of hybridization. In general, "stringent hybridization" is performed at about 25° C. below the thermal melting point (T m) for the specific DNA hybrid under a particular set of conditions. "Stringent washing" is performed at temperatures about 5° C. lower than the T m for the specific DNA hybrid under a particular set of conditions. The T m is the temperature at which 50% of the target sequence hybridizes to a perfectly matched probe. See Sambrook et al., p. 9.51.

In general, the T m decreases by 1–1.5° C. for each 1% of mismatch between two nucleic acid sequences. Thus, one having ordinary skill in the art can alter hybridization and/or washing conditions to obtain sequences that have higher or lower degrees of sequence identity to the target nucleic acid. For instance, to obtain hybridizing nucleic acids that contain up to 10% mismatch from the target nucleic acid sequence, 10–15° C. would be subtracted from the calculated T m of a perfectly matched hybrid, and then the hybridization and washing temperatures adjusted accordingly. Probe sequences may also hybridize specifically to duplex DNA under certain conditions to form triplex or other higher order DNA complexes. The preparation of such probes and suitable hybridization conditions are well known in the art.

An example of stringent hybridization conditions for hybridization of complementary nucleic acid sequences having more than 100 complementary residues on a filter in a Southern or Northern blot or for screening a library is 50% formamide/6×SSC at 42° C. for at least ten hours. Another example of stringent hybridization conditions is 6×SSC at 68° C. for at least ten hours. An example of low stringency hybridization conditions for hybridization of complementary nucleic acid sequences having more than 100 complementary residues on a filter in a Southern or northern blot or for screening a library is 6×SSC at 42° C. for at least ten hours. Hybridization conditions to identify nucleic acid sequences that are similar but not identical can be identified by experimentally changing the hybridization temperature from 68° C. to 42° C. while keeping the salt concentration constant (6×SSC), or keeping the hybridization temperature and salt concentration constant (e.g. 42° C. and 6×SSC) and varying the formamide concentration from 50% to 0%. Hybridization buffers may also include blocking agents to lower background. These agents are well-known in the art. See Sambrook et al., pp. 8.46 and 9.46–9.58.

Wash conditions also can be altered to change stringency conditions. An example of stringent wash conditions is a 0.2×SSC wash at 65° C. for 15 minutes (see Sambrook et al., for SSC buffer). Often the high stringency wash is preceded by a low stringency wash to remove excess probe. An exemplary medium stringency wash for duplex DNA of more than 100 base pairs is 1×SSC at 45° C. for 15 minutes. An exemplary low stringency wash for such a duplex is 4×SSC at 40° C. for 15 minutes. In general, signal-to-noise ratio of 2× or higher than that observed for an unrelated probe in the particular hybridization assay indicates detection of a specific hybridization.

As defined herein, nucleic acids that do not hybridize to each other under stringent conditions are still substantially homologous to one another if they encode polypeptides that are substantially identical to each other. This occurs, for example, when a nucleic acid is created synthetically or recombinantly using a high codon degeneracy as permitted by the redundancy of the genetic code.

In another embodiment, antibodies that bind to the polypeptide of SEQ ID NO:2, or fragments thereof, are provided. The polypeptides of this invention may be used to elicit polyclonal or monoclonal antibodies. Antibodies directed against the polypeptides of this invention are immunoglobulin molecules or portions thereof that are immunologically reactive with the polypeptide of the present invention. It should be understood that the antibodies of this invention include antibodies immunologically reactive with fusion proteins. Antibodies directed against a polypeptide of the invention may be generated by immunization of a mammalian host.

The term "antibody" refers to a polypeptide encoded by an immunoglobulin gene, genes, or fragments thereof. The immunoglobulin genes include the kappa, lambda, alpha, gamma, delta, epsilon and mu constant regions, as well as a myriad of immunoglobulin variable regions. Light chains are classified as either kappa or lambda. Heavy chains are classified as gamma, mu, alpha, delta, or epsilon, which in turn define the immunoglobulin classes IgG, IgM, IgA, IgD and IgE, respectively. An antibody can be polyclonal or monoclonal.

Antibodies exist for example, as intact immunoglobulins or as a number of well-characterized fragments produced by digestion with various peptidases. For example, trypsin digests an antibody below the disulfide linkages in the hinge region to produce F(ab)$_2$, a dimer of Fab which itself is a light chain joined to a V H—C H 1 by a disulfide bond. See Paul, ed. (1993) Fundamental Immunology, Third Edition (New York: Raven Press), for a detailed description of epitopes, antibodies and antibody fragments. One of skill in the art recognizes that such Fab fragments may be synthesized de novo either chemically or using recombinant DNA technology. Thus, as used herein, the term antibody includes antibody fragments produced by the modification of whole antibodies or those synthesized de novo. The term antibody also includes single-chain antibodies, which generally consist of the variable domain of a heavy chain linked to the variable domain of a light chain. The production of single-chain antibodies is well known in the art (see, e.g., U.S. Pat. No. 5,359,046). The antibodies of the present invention are optionally derived from libraries of recombinant antibodies in phage or similar vectors (see, e.g., Huse et al. (1989) Science 246:1275–81; Ward et al. (1989) Nature 341:544–46; Vaughan et al. (1996) Nature Biotech. 14:309–14).

As used herein, "epitope" refers to an antigenic determinant of a polypeptide, i.e., a region of a polypeptide that provokes an immunological response in a host. This region need not comprise consecutive amino acids. The term epitope is also known in the art as "antigenic determinant." An epitope may comprise as few as three amino acids in a spatial conformation which is unique to the immune system of the host. Generally, an epitope consists of at least five such amino acids, and more usually consists of at least 8–10 such amino acids. Methods for determining the spatial conformation of such amino acids are known in the art.

In another embodiment, compositions comprising polypeptide of the invention are provided. Such compositions are suitable for introducing the polypeptide in to a marine organism. The compositions of this invention may be in a variety of forms, which may be selected according to the preferred modes of administration. These include, for example, solid, semi-solid and liquid forms such as tablets, pills, powders, liquid solutions or suspensions, suppositories, and injectable and infusible solutions. The preferred form depends on the intended mode of administration and application. Modes of administration may include oral, parenteral, subcutaneous, intravenous, intralesional or topical administration. In one aspect, the composition can be administered as an additive in the food source of a target marine organism, such as an organism from the genus *Epinephelus*.

In another embodiment, methods for regulating reproduction, gonad differentiation, or sex reversal in a marine organism are provided. The methods encompass administering a polypeptide of the invention to a target marine organism.

In another embodiment, novel nucleic acids are provided. The invention provides an isolated nucleic acid encoding a polypeptide comprising the amino acid sequence of SEQ ID NO:2 containing up to 10 conservative amino acid substitutions. The invention further provides an isolated nucleic acid comprising the nucleotide sequence represented by SEQ ID NO:1 or SEQ ID NO:12.

Also provided are isolated nucleic acids that hybridizes under highly stringent conditions with a nucleic acid consisting of the nucleotide sequence represented by SEQ ID NO:1 or SEQ ID NO:12. Hybridization conditions for nucleic acids are described above.

The invention further provides isolated nucleic acids that are at least 90%, 95% or 98% identical to the nucleic acid sequence represented by SEQ ID NO:1 or SEQ ID NO:12. The nucleic acids of this invention may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

"Conservatively modified variations" of a particular nucleic acid sequence refers to nucleic acids that encode identical or essentially identical amino acid sequences or DNA sequences where no amino acid sequence is encoded. Due to the degeneracy of the genetic code, a large number of functionally identical nucleic acids encode any given polypeptide sequence. When a nucleic acid sequence is changed at one or more positions with no corresponding change in the amino acid sequence which it encodes, that mutation is called a "silent mutation." Thus, one species of a conservatively modified variation according to this invention is a silent mutation. Accordingly, every nucleic acid sequence herein which encodes a polypeptide also describes every possible silent mutation or variation.

It is envisioned that the nucleic acid and amino acid sequences described herein may be compared to other vertebrate sequences, including human and non-human mammalian sequences, as well as plant and insect sequences using any one of the large number of programs known in the art for comparing nucleotide and amino acid sequences to sequences in a database. Examples of such programs are Fasta and blastp, discussed above. Examples of databases which can be searched include GenBank-EMBL, SwissProt, DDBJ, GeneSeq, and EST databases, as well as databases containing combinations of these databases.

In another embodiment, vectors comprising the nucleic acid sequence of the invention are provided. In one aspect, the vector is an expression vector. DNA sequences may be expressed by operatively linking them to an expression control sequence in an appropriate expression vector and employing that expression vector to transform an appropriate unicellular host. Expression control sequences are sequences which control the transcription, post-transcriptional events and translation of DNA sequences. Such operative linking of a DNA sequence of this invention to an expression control sequence, of course, includes, if not already part of the DNA sequence, the provision of a translation initiation codon, ATG, in the correct reading frame upstream of the DNA sequence.

A wide variety of host/expression vector combinations may be employed in expressing the nucleic acid sequences of this invention. Useful expression vectors, for example, may consist of segments of chromosomal, non-chromosomal and synthetic DNA sequences.

Useful expression vectors for bacterial hosts include bacterial plasmids, such as those from $E.$ $coli$, including pBluescript, pGEX-2T, pUC vectors, col E1, pCR1, pBR322, pMB9 and their derivatives, wider host range plasmids, such as RP4, phage DNAs, e.g., the numerous derivatives of phage lambda, e.g., NM989, GT10 and GT11, and other phages, e.g., M13 and filamentous single stranded phage DNA. In yeast, vectors include Yeast Integrating plasmids (e.g., YIp5) and Yeast Replicating plasmids (the YRp and YEp series plasmids), Yeast centromere plasmids (the YCp series plasmids), pGPD-2, plasmids and derivatives thereof, and improved shuttle vectors such as those described in Gietz& Sugino (1988) Gene 74:527–34 (YIplac, YEplac and YCplac). Expression in mammalian cells can be achieved using a variety of plasmids, including pSV2, pBC12BI, and p91023, as well as lytic virus vectors (e.g., vaccinia virus, adeno virus, and baculovirus), episomal virus vectors (e.g., bovine papillomavirus), and retroviral vectors (e.g., murine retroviruses). Useful vectors for insect cells include baculoviral vectors and pVL 941.

Given the strategies described herein, one of skill in the art can construct a variety of vectors and nucleic acid molecules comprising functionally equivalent nucleic acids. DNA cloning and sequencing methods are well known to those of skill in the art and are described in an assortment of laboratory manuals, including Sambrook et al., 1989; and Ausubel et al., 1994 Supplement.

In yet another embodiment, host cells comprising a vector of the invention are provided. Transformation and other methods of introducing nucleic acids into a host cell (e.g., transfection, electroporation, liposome delivery, membrane fusion techniques, high velocity DNA-coated pellets, viral infection and protoplast fusion) can be accomplished by a variety of methods which are well known in the art (see, for instance, Ausubel, supra, and Sambrook, supra). Bacterial, yeast, plant or mammalian cells are transformed or transfected with an expression vector, such as a plasmid, a cosmid, or the like, wherein the expression vector comprises the DNA of interest. Alternatively, the cells may be infected by a viral expression vector comprising the DNA or RNA of interest. Depending upon the host cell, vector, and method of transformation used, transient or stable expression of the polypeptide will be constitutive or inducible. One having ordinary skill in the art will be able to decide whether to express a polypeptide transiently or stably, and whether to express the protein constitutively or inducibly.

In another embodiment, methods for producing a reproduction regulator 1 polypeptide using a host cell of the invention are provided. A wide variety of unicellular host cells are useful in expressing the DNA sequences of this invention. These hosts may include well known eukaryotic and prokaryotic hosts, such as strains of $E.$ $coli$, $Pseudomonas,$ $Bacillus,$ $Streptomyces$, fungi, yeast, insect cells such as $Spodoptera$ $frugiperda$ (SF9), animal cells such as CHO, BHK, MDCK and various murine cells, e.g., 3T3 and WEHI cells, African green monkey cells such as COS 1, COS 7, BSC 1, BSC 40, and BMT 10, and human cells such as VERO, WI38, and HeLa cells, as well as plant cells in tissue culture.

The polypeptides of this invention may be fused to other molecules, such as genetic, enzymatic or chemical or immunological markers such as epitope tags. Fusion partners include, inter alia, myc, hemagglutinin (HA), GST, immunoglobulins, β-galactosidase, biotin trpE, protein A, β-lactamase, α amylase, maltose binding protein, alcohol dehydrogenase, polyhistidine (for example, six histidine at the amino and/or carboxyl terminus of the polypeptide), lacZ, green fluorescent protein (GFP), yeast a mating factor, GAL4 transcription activation or DNA binding domain, luciferase, and serum proteins such as ovalbumin, albumin and the constant domain of IgG. See, e.g., Godowski et al. (1988) Science 241(4867):812–6; and Ausubel et al., supra. Fusion proteins may also contain sites for specific enzymatic cleavage, such as a site that is recognized by enzymes such as Factor XIII, trypsin, pepsin, or any other enzyme known in the art. Fusion proteins will typically be made by either recombinant nucleic acid methods, as described above, chemically synthesized using techniques such as those described in Merrifield, et al. (1965) Nature 207(996): 522–3, or produced by chemical cross-linking.

In another embodiment, an array comprising a plurality of addresses, wherein at least one address has disposed thereon the nucleic acid of SEQ ID NO:1 or SEQ ID NO:12, or fragment of SEQ ID NO:1 or SEQ ID NO:12, is provided. In yet another embodiment, an array comprising a substrate comprising a plurality of addresses, wherein at least one address has disposed thereon a biomolecule that binds to a polypeptide of the invention, is provided. The biomolecule can be, for example, an antibody or a receptor.

The term "array," as used herein, generally refers to a predetermined spatial arrangement of binding islands, biomolecules, or spatial arrangements of binding islands or biomolecules. Arrays according to the present invention that include biomolecules immobilized on a surface may also be referred to as "biomolecule arrays." Arrays according to the present invention that comprise surfaces activated, adapted, prepared, or modified to facilitate the binding of biomolecules to the surface may also be referred to as "binding arrays." Further, the term "array" may be used herein to refer to multiple arrays arranged on a surface, such as would be the case where a surface bore multiple copies of an array. Such surfaces bearing multiple arrays may also be referred to as "multiple arrays" or "repeating arrays." The use of the term "array" herein may encompass DNA chips, biomolecule arrays, binding arrays, multiple arrays, and any combination thereof; the appropriate meaning will be apparent from context.

A number of embodiments of the invention have been described. Nevertheless, it will be understood that various modifications may be made without departing from the spirit and scope of the invention. For example:

EXAMPLE 1

Extraction of RNA and Construction of SMART cDNA Plasmid Library

The total RNA of the pituitary was extracted using a SV Total RNA Isolation System (Promega). Kit (SV Total RNA Isolation System, Promega) is offered all reagents used in this study. The detailed steps were following: a specimen of *E. coioides* weighted about 500 g was anaesthetized and bled to open the skull and take out the pituitary, then 175 µl extraction buffer was added; after mixed thoroughly, 350 µl RNA dilution buffer was added, mixed and blocked for 3 minutes at 70° C., then centrifuged for 10 minutes at 14000×g. The supernatant was transferred and 200 µl 95% ethanol was added, transferred to the centrifuged column after pipetting thoroughly, centrifuged for 10 minutes at 14000×g, then 600 µl RNA washing buffer was added and centrifuged for 10 minutes at 14000×g. 200 µl DNase stopping buffer was added after adding 50 µl DNase I (Promega) to digest for 15 minutes at 20–25° C., then centrifuged for 1 minute at 14000×g. Next, 600 µl SV RNA washing buffer was added, and the mixture was centrifuged for 1 minute at 14000×g, then 250 µl RNA washing buffer was added again and centrifuged for 2 minutes at high speed. The total RNA was washed twice with 250 µl RNase-free water. 0.5–5 µl sample was used to detect the concentration and quality of the total RNA. The rest total RNA was frozen at −70° C., condensed to dryness with a vacuum lyophilizer at a super low temperature, then dissolved in 20–30 µl water and 0.5 µl sample was used for electrophoresis to detect the concentration and quality of mRNA.

A SMART cDNA library construction Kit (Clontech) was used to synthesize SMART cDNA, the detailed steps were as follows: three primers used in the synthesis were as follows: (1) CDS primer (10 µmol/L) 5'-AAGCAGTGGTAA-CAACGCAGAGTACT$_{30}$)NN-3' (SEQ ID NO: 3); (2) Smart II oligonucleotide (10 µmol/L) 5'-AAG CAGTGGTAA-CAACGCAGAGTACGCGGG-3' (SEQ ID NO: 4); (3) PCR primer (10 µmol/L) 5'-AAGCAG TGGTAACAACGCA-GAGT-3' (SEQ ID NO: 5).

The first strand of cDNA was synthesized according to the library construction method with 50 ng total RNA of the pituitary: 1 µl CDS primer and Smart II oligonucleotide were added, incubated for 2 minutes at 72° C., then cooled quickly for 2 minutes on the ice. Then, 2 µl 5× first strand buffer (250 mmol/L Tris-HCl, pH8.3; 375 mmol/L KCl; 30 mmol/L MgCl$_2$), 1 µl DTT (20 mmol/L), 1 µl dNTPs (10 mmol/L) and 1 µl PowerScript reverse transcriptase were added into the reaction system of 10 µL final volume, and incubated for 1 hour at 42° C. to synthesize the first strand of cDNA. Then, 2 µl dNTPs, 4 µl PCR primers and 2 µl 50× Advantage 2 cDNA Polymerase mix were added to 2 µl first strand of cDNA to perform PCR in 100 µl reaction system: initial denaturation was performed for 1 minute at 95° C., followed by 13 cycles of 5 seconds at 95° C., 5 seconds at 65° C., and 6 minutes at 68° C., with a final elongation of 8 minutes at 72° C. After reaction, 5 µL PCR products were detected by electrophoresis. The PCR products were used to construct the plasmid library. The synthesized SMART cDNA was linked to pEGM®-T vector (Promega), then transformed into DH5α competent cells.

EXAMPLE 2

Random Screening of the Plasmid Library and Sequencing

The transformation culture was plated onto the antibiotic plates (the plates contained 100 µg/mL Amp, X-gal (0.027%) and IPTG (0.047%)) and incubated at 37° C. overnight. White colonies were selected and put into an eppendorf tube with 100 µL Amp-LB, then cultured over 2 hours at 37° C. PCR was used to identify the size of the inserted fragment with 1 µL strain solution as the template, and M13+/M13− as the primers (M13+: CAGGAAA-CAGCT ATGAC (SEQ ID NO: 6); M13−: GTAAAC-GACGGCCAGT (SEQ ID NO: 7)). PCR amplifications were performed in a Perkin-Elmer DNA GeneAmp PCR System 9600. Amplification reactions were performed in volume of 20 µl containing approximately 1 µl cultured content as template DNA, 0.2 µM of each primer, 0.5 units of Taq polymerase (Biostar International, Canada), 0.1 µM of each dNTP, 1× Buffer for Taq polymerase (Biostar International, Canada). With an initial denaturation at 94° C. for 4 min, followed by 32 cycles of 40 seconds at 94° C., 50 seconds at 55° C., 1.5 min at 72° C. and a final extension at 72° C. for 7 minutes. The colonies with the inserted fragments of more than 500 bp were sequenced (Shanghai, Sangon Corporation).

Five colonies were detected to contain the said gene in 90 randomly screened and sequenced colonies (the number was 3-27, 3-46, 3-69, 3-84 and 3-103, respectively). The cDNA of the gene is 560 bp long with an open reading frame of 192 bp (31–222) starting from the vertebrate initiation codon comprised in a motif of ANNATG, which encodes 63 amino acids, and the 5' non-coding region is 30 bp long; the 3' non-coding region is 338 bp long with a polyA tailing signal (AAUAAA) and a polyA tail. The gene has no homology with other genes and is a new gene through homology search in the GenBank.

EXAMPLE 3

Extraction of the total RNA from Tissues and Embryos and RT-PCR Reaction

RNA was extracted from some kinds of tissues of *E. coioides* (including liver, kidney, spleen, pancreas, heart, muscle, pituitary, hypothalamus, endbrain, cerebel, midbrain and medulla oblongata), brain pituitary, hypothalamus and mature ovary during the different stages, for example, oogenesis stage, oocyte mature stage and the sex reversal stage and from the gonad during the sex reversal stage, also the total RNA was extracted from the different embryo development stages of *E. coioides* (including unfertilized egg, morula, blastula, gastrula, neurula, optic vesicle stage embryo, heartbeat beginning stage embryo, embryo prior to hatching, hatching embryo, one day hatched fry). The total RNA was extracted with SV total RNA isolation system (Promega). The detailed steps were as above. The first strand of cDNA was synthesized with 0.2 μg of each of total RNA, M-MLV reverse transcriptase (Gibco BRL) and oligo(dT)$_{8-12}$. PCR was performed with 1 μl of the first strand of cDNA diluted 10 times as the template and the specific primers of the gene (3-46-F:GA ATT CAT ATG AAG GGA CTG AGC TTG GTT C (SEQ ID NO: 8) and 3-46-R: GCTC GAG CTA AGA CCG CAC AGC ACA GC (SEQ ID NO: 9). The total volume of the reaction system was 20 μl, which included 1 μl template DNAs, 0.2 μM primers, 0.5 U Taq polymerase, 0.1 μM dNTPs and 1× Taq polymerase buffer. PCR reactions were performed in a DNA GeneAmp PCR System 9600 Thermal Cycler (Perkin-Elmer), and the reaction program was following: initial denaturation for 4 minutes at 94° C., followed by 28 cycles of 40 seconds at 94° C., 50 seconds at 62° C., and 50 seconds at 72° C., with a final elongation of 7 minutes at 72° C. The PCR products were isolated by 1% agarose electrophoresis. The α-tubulin gene of the crucian was used as the control upper primer: 5'-GTG-CACTGGTCTTCA GGGGTT-3' (SEQ ID NO: 10), down primer: 5'-GGGAAGTGGATGCGTGGGTAT-3' (SEQ ID NO: 11)).

Figure 4:
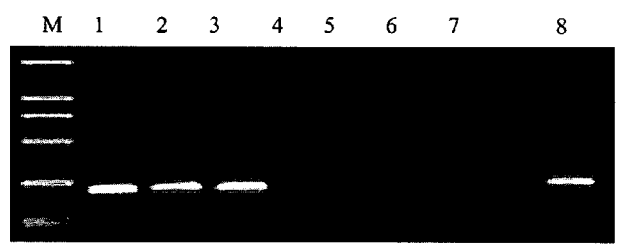
FIG. 4 illustrates the expression of rr1 gene in the pituitary, hypothalamus and mature ovary during the different stages of E. coioides development—the oogenesis stage, oocyte mature stage and the sex reversal stage, and in the gonad during the sex reversal stage, 1: pituitary of individual at the oogenesis stage, 2: pituitary of individual at the oocyte mature stage, 3: pituitary of individual at the sex reversal stage, 4: hypothalamus of individual at the oogenesis stage, 5: hypothalamus of individual at the oocyte mature stage, 6: hypothalamus of individual at the sex reversal stage, 7: ovary, 8: gonad during sex reversal.
Figure 5:
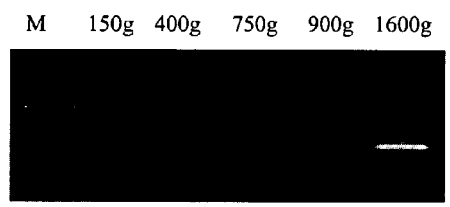
FIG. 5 shows the expression of rr1 gene in the gonad of E. coioides weighted 150 g, 450 g, 700 g, 950 g and 1600 g respectively detected by RT-PCR.
Figure 6:
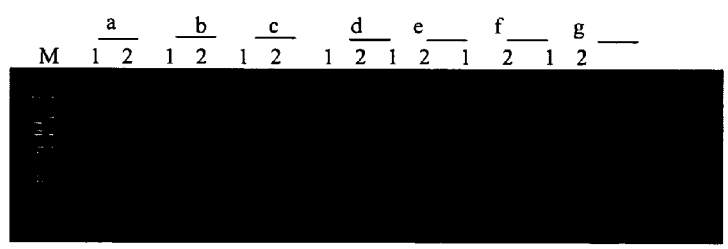
FIG. 6 shows the expression of rr1 gene in the gonad of E. coioides during the artificial sex reversal process detected by RT-PCR, a: before administrating the hormone, b: one week, c: two weeks, d: three weeks, e: four weeks, f: five weeks, g: six weeks.

PCR performed with α-tubulin primers confirmed that the efficiency of reverse transcription in each tissue and each embryo development stage was adequate and the quantity of cDNA was almost equal. The expression pattern of the gene indicated that the gene was strongly transcribed in the pituitary, was less strongly transcribed in the hypothalamus, and no mRNA was detected in ten other tissues examined (FIG. 4). The same high abundance was seen in the pituitary during three different gonad development stages. The same low abundance in the hypothalamus was detected in all three stages, and no mRNA was detected in the mature ovary. However, there was a highly expressed transcript in the gonad during the sex reversal stage as will be seen from FIG. 5. No expression of the gene was detected in the embryo development stage.

EXAMPLE 4

Preparation of rr1 Gene Fusion Protein

The rr1 cDNA coding 63 residues was amplified by PCR using primers (3-46-F: GA ATT CAT ATG AAG GGA CTG AGC TTG GTT C(SEQ ID NO: 8) (3-46-R: GCTC GAG CTA AGA CCG CAC AGC ACA GC(SEQ ID NO: 9)). The PCR condition was same as the condition of RT-PCR reaction. Primer 3-46-F includes site of EcoR I and start coden (ATG). Primer 3-46-R includes site of Xol I and stop coden (TAG).

After running products of PCR reactions in 1% agarose gel, the selected DNA fragments were excised and put into 1.5 ml tubes. The DNA fragments were purified by Biostar Glassmilk DNA Purification Kit (BioStar International, Canada). Kit is offered all reagents used in this study. Briefly, the tubes were added 3 volumes of NaI and incubated at 55° C. to melt gel. Glassmilk was suspended well and 5 μl glassmilk is added into the tubes. Mixing and incubating at room temperature for 5 minutes, DNA was bound to glassmilk. Glassmilk/DNA complex was pelleted by spin for 5 seconds in full speed. The supernatant was discarded and the glassmilk/DNA was resuspended in 0.5 ml cold Wash Buffer. Spin again and repeat washing pellet for additional two times. The supernatant was discarded and the pellet was dried at room temperature for about 10 minutes. 10 μl deionized water was added and the pellet was resuspended well and then centrifuged for 30 seconds. The supernatant contained the eluted DNA was taken carefully and used directly for ligation.

Ligation reactions were performed in volume 10 μl containing approximately 50 ng pure DNA, 50 ng pGEM®-T Easy Vector (Promega), 1 μl T4 DNA ligase (3 Weiss units/μl, Promega) and incubated overnight at 4° C. Ligation reactions were transferred into the tube containing DH5α High Efficiency Competent Cells. The tubes gently were flicked to mix and placed on ice for 20 minutes. After heat shocking the cells for 40–50 seconds in a water bath at exactly 42° C., the tubes were placed on ice for 2 minutes. Add 1 ml LB medium to tubes and incubate for 1.5 hours at 37° C. with shaking (150 rpm). The cells were pelleted by centrifugation, resuspended in 100 μl LB medium and plated on plates containing LB/ampicillin (50 μg/ml). Incubate the plates overnight at 37° C.

Select white colonies and put into tubes containing 4.5 ml LB and ampicillin and incubate overnight at 37° C. (150 rpm). The pure plasmid DNA was obtained by using Min-M™ Plasmid Miniprep (Viogene) according to manufacturer protocol. Kit (Min-M™ Plasmid Miniprep Viogene) is offered all reagents used in this study. Briefly, 5 ml obtained cultures were span 4000 g for 5 minutes to pellet cells. After adding 250 μl solution I (suspension) cell), solution II (lysis), solution III (neutralization), the tubes were span 10,000 g for 5 minutes. The supernatants were put into a column and span 10,000 g for 5 seconds. Add 0.5 ml wash I buffer and span 100,00 g for 30 seconds. After discarding the supernatant, 0.7 ml wash II buffer was added, then spanned at 10,000 g for 30 seconds. 50 μl deionized water was added to column, stand for 30 seconds and span 10,000 g for 1 minute.

Figure 7:
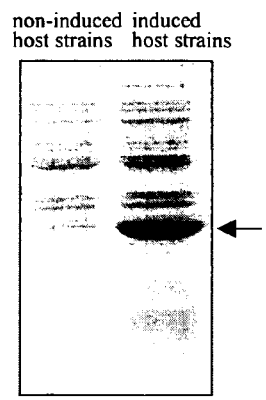
FIG. 7 shows the RR1 fusion protein expressed in BL21 (DE3) pLysS, the RR1 fusion protein is indicated by arrow.
Figure 8:
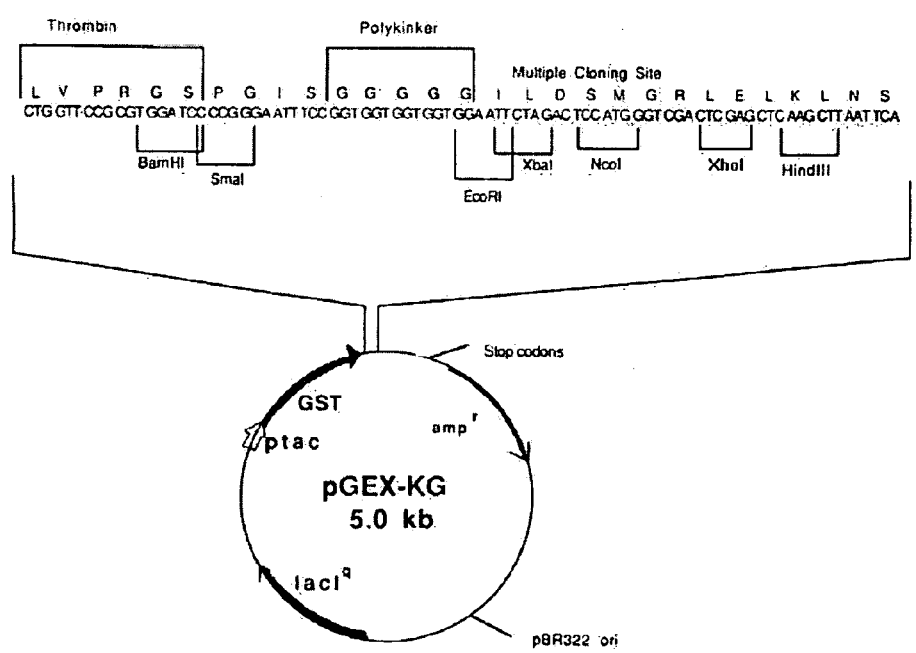
FIG. 8 shows the express vector pGEX-KG.

The pure plasmid DNA containing rr1 cDNA fragments and Pgex-KG vector were double-digested with EcoR I (Biolabs) Xol I (Biolabs), respectively at 37° C. After running products of digested reactions in 1% agarose gel, the selected DNA fragments were excised and put into 1.5 ml tubes. The DNA fragments were purified by Biostar Glassmilk DNA Purification Kit (BioStar International, Canada). Then the pure plasmid DNA containing rr1 cDNA fragments and pGEX☐KG vector were used directly for ligation. Ligation reactions were performed in volume 10 μl containing approximately 50 ng plasmid DNA, 50 ng pGEX-KG Vector, 1 μl T4 DNA ligase (3 Weiss units/μl) and incubated overnight at 4° C. The expressed vector pGEX-KG-rr1 was constructed and was transferred into the tube containing BL21(DE3) pLysS(Novagen), which plated on LB/ampicillin (50 μg/ml) plates. Incubate the plates overnight at 37° C. Select white colonies and put into tubes containing 4.5 ml LB and 50 μg/ml ampicillin and incubate overnight at 37° C. Morrow, using 400 μl overnight cultures inoculate 4 ml of fresh LB/ampicillin (50 μg/ml). Grow the culture for 2 hours at 37° C. The optical density $OD_{600}$ will be between 0.6–0.8. Induce the expression of the fusion protein by adding IPTG to 1 mM final concentration and incubate 3–6 hours at 37° C. Centrifuge the samples at maximum speed in a microcentrifuge for 30 seconds. Remove and discard the supernatant solution. Resuspend the cell pellet in 200 μl of 2× Laemmli protein sample buffer (per 10 milliliters, combine: 2.5 ml 0.5M Tris, pH6.8, 4 ml 10% SDS, 2 ml glycerol, 1 mlβ-mercaptoethanol, 0.01% (w/v) bromophenol blue). Ultrasonic break up cell and microcentrifuge (12000 g) to collect supernatant solution. Make a 12.5% SDS-PAGE gel. Load 20 μl of sample on the SDS-PAGE gel and run the gel for approximately 45 minutes to separate the proteins, and stain the gel with Coomassie Brilliant Blue. The expressed rr1 protein is soluble (FIG. 7).

Accordingly, other embodiments are within the scope of the following claims.

What is claimed is:

1. An isolated polypeptide, the sequence of which consists of the amino acid sequence of SEQ ID NO:2, is found in the pituitary of a vertebrate.

2. An isolated polypeptide comprising the amino acid sequence of SEQ ID NO:2.

3. The polypeptide of claim 1, wherein the vertebrate is from the genus *Epinephelus*.

4. The polypeptide of claim 3, wherein the vertebrate is *Epinephelus coioides*.

5. A composition comprising the polypeptide of claim 1 or 2, wherein the composition is suitable for introducing said polypeptide into a marine organism.

6. An additive for an artificial bait, comprising the composition of claim 5 included in an artificial bait.

7. The composition of claim 5, wherein the marine organism is from the genus *Epinephelus*.

8. The composition of claim 7 wherein the marine organism is *Epinephelus coloides*.

9. A method for regulating reproduction in a marine organism, the method comprising contacting the organism with the polypeptide of claim 1.

10. A method for regulating gonad differentiation in a marine organism, the method comprising contacting the organism with the polypeptide of claim 1.

11. A method for regulating sex reversal in a marine organism, the method comprising contacting the organism with the polypeptide of claim 1.

12. The method of claim 9, 10, or 11, wherein the marine organism is from the genus *Epinephelus*.

13. The method of claim 12, wherein the marine organism is *Epinephelus coioides*.

14. A method for regulating reproduction in a marine organism, the method comprising contacting the organism with the polypeptide of claim 2.

15. A method for regulating gonad differentiation in a marine organism, the method comprising contacting the organism with the polypeptide of claim 2.

16. A method for regulating sex reversal in a marine organism, the method comprising contacting the organism with the polypeptide of claim 2.

17. The method of claim 14, 15, or 16, wherein the marine organism is from the genus *Epinephelus*.

18. The method of claim 17, wherein the marine organism is *Epinephelus coioides*.

* * * * *